(12) United States Patent
Novak et al.

(10) Patent No.: US 11,986,433 B2
(45) Date of Patent: May 21, 2024

(54) SHOCK WAVE APPARATUS

(71) Applicant: STORZ MEDICAL AG, Tägerwilen (CH)

(72) Inventors: Pavel Novak, Stetten (CH); Manfred Schulz, Tägerwilen (CH); Stephan Swart, Moers (DE); Carlo DiMaio, Duisburg (DE)

(73) Assignee: Storz Medical AG, Taegerwilen (CH)

( * ) Notice: Subject to any disclaimer, the term of this patent is extended or adjusted under 35 U.S.C. 154(b) by 1010 days.

(21) Appl. No.: 16/603,650

(22) PCT Filed: Apr. 12, 2018

(86) PCT No.: PCT/EP2018/059379
§ 371 (c)(1),
(2) Date: Oct. 8, 2019

(87) PCT Pub. No.: WO2018/189285
PCT Pub. Date: Oct. 18, 2018

(65) Prior Publication Data
US 2020/0113777 A1    Apr. 16, 2020

(30) Foreign Application Priority Data

Apr. 12, 2017 (EP) ...................... 17020149

(51) Int. Cl.
*A61H 23/00* (2006.01)
*A61B 17/225* (2006.01)
(Continued)

(52) U.S. Cl.
CPC ....... *A61H 23/008* (2013.01); *A61B 17/2251* (2013.01); *A61H 23/04* (2013.01);
(Continued)

(58) Field of Classification Search
CPC .................. A61H 23/008; A61H 23/04; A61H 2201/1664; A61H 2201/169;
(Continued)

(56) References Cited

U.S. PATENT DOCUMENTS

| 5,941,838 A | 8/1999 | Eizenhofer |
| 2005/0209586 A1* | 9/2005 | Menne ............. A61B 17/22004 606/1 |

(Continued)

FOREIGN PATENT DOCUMENTS

| DE | 197 25 477 A1 | 12/1998 |
| DE | 102 15 416 A1 | 10/2003 |

(Continued)

OTHER PUBLICATIONS

International Search Report and Written Opinion dated Oct. 18, 2018.
IPRP and Written Opinion dated Oct. 15, 2019.

*Primary Examiner* — Quang D Thanh
(74) *Attorney, Agent, or Firm* — Wood, Phillips, Katz, Clark & Mortimer

(57) ABSTRACT

The invention relates to a shock wave apparatus for treating the human or animal body with an applicator which is intended to couple strokes into the body and has a hollow shape at a front area intended to be placed on the body and a relatively soft elastomeric material with a maximum Shore A hardness of 60 Sh.

16 Claims, 3 Drawing Sheets

(51) Int. Cl.
*A61H 23/04* (2006.01)
*A61B 17/00* (2006.01)
(52) U.S. Cl.
CPC ............... *A61B 2017/00544* (2013.01); *A61H 2201/1664* (2013.01)
(58) Field of Classification Search
CPC ...... A61B 17/2251; A61B 2017/00544; A61B 17/225; A61B 2017/00862; A61B 2017/22025
See application file for complete search history.

(56) References Cited

U.S. PATENT DOCUMENTS

| | | | | |
|---|---|---|---|---|
| 2010/0256535 | A1* | 10/2010 | Novak | A61H 23/008 601/4 |
| 2011/0054367 | A1* | 3/2011 | Schulz | A61H 23/008 601/46 |
| 2014/0350438 | A1 | 11/2014 | Papirov et al. | |
| 2017/0209708 | A1* | 7/2017 | Schwarz | A61N 2/004 |
| 2017/0304144 | A1* | 10/2017 | Tucker | A61H 7/005 |

FOREIGN PATENT DOCUMENTS

| | | |
|---|---|---|
| DE | 20 2004 011 323 U1 | 9/2005 |
| EP | 2 095 843 A1 | 9/2009 |
| WO | 2014036170 A1 | 3/2014 |

\* cited by examiner

SHOCK WAVE APPARATUS

CROSS-REFERENCE TO RELATED APPLICATIONS

This application claims priority of European Appln. No. 17020149.5, filed Apr. 12, 20174 and Appln. No. PCT/EP2018/059379, filed Apr. 12, 2018, the disclosures of which are hereby incorporated by reference in their entirety.

FIELD OF THE INVENTION

The present invention relates to an apparatus for treating the human or animal body by applying strokes to the surface of the body. For the purposes of simplification, reference will be made below to the body of a patient which is preferably human.

BACKGROUND OF THE INVENTION

In the prior art, different apparatuses of the basic type described are known. DE 197 25 477 C describes such an apparatus for instance, wherein a shock wave is initiated by the collision of a pneumatically accelerated striking member or projectile with an impact body or applicator initially at rest, wherein the shock wave can be coupled into the body of the patient when a front area of the applicator is placed on the patient's body at the time of the collision. As regards the history of its development, this type of apparatus results from lithotripsy apparatuses which can be used for transferring such a shock wave onto a kidney stone or similar for a disintegration of said kidney stone or similar, for instance via a long rod-like probe at the front area of the applicator.

The emphasis when describing this is in each case on the shock wave created by the collision, which can be more or less comparable to an actual shock wave generated by a classic, usually focusing lithotripsy apparatus having, for instance, a piezoelectric or electromagnetic actuator. Such shock waves can have rising edges with a width in the region of a few µs and an amplitude in a lower double-digit MPa region (for instance 2 µs and 15 MPa measured 1 cm in front of the front area). In the document cited, however, it is emphasised that the macroscopic movement of the applicator's centre of mass, which cannot be prevented as such physically, shall be kept as small as possible because it is considered as disadvantageous.

As a second example, reference is made to DE 20 2004 011 323 U and, with very similar content, US 2011/0054367 A1. There, an apparatus which is similar in terms of its technical design, is described, with the elastic mounting of the applicator in the housing being adapted for a larger movement of the applicator's centre of mass ("travel"), however. There, it is emphasised that a therapeutic effect can be caused also or primarily by the actual macroscopic strokes (namely as a result of the travel), which also depends on the indication.

SUMMARY OF THE INVENTION

In general, the present invention relates to apparatuses of that type, namely regarding the application of shock waves as well as regarding the application of "macroscopic strokes" of the applicator to the body surface.

The object of the present invention is to provide such an apparatus with further possible applications on the surface of the patient's body.

According to the invention, this object is solved by means of an apparatus for treating a human or animal body, having an applicator for placing on said body from the outside, a housing in which said applicator is held, and a mechanism for generating strokes of said applicator relative to said housing in a stroke direction such that said strokes can be coupled into said body when said applicator is placed on said body, characterised in that said applicator has a front face facing forwards in the stroke direction, adapted to be placed onto said body, having a hollow shape and consisting of an elastomeric material having a maximum Shore hardness of 60 Sh at said hollow shape at least, wherein said elastomeric material has a thickness at said hollow shape in said stroke direction of at least 3 mm, wherein 5 mm, 7 mm and 10 mm are preferred as a lower limit.

Preferred embodiments of the device according to the invention and a corresponding use are specified in the dependent claims. The features contained in these dependent claims and also the disclosure of the description below are generally to be understood with respect to both invention categories, without an explicit distinction between the two always being made in specific cases.

The basic idea behind the invention consists in designing the applicator applying the strokes to the body to be treated so that the front area to be placed on the body is hollow and particularly soft. According to what the inventor found, this means that the applicator can be placed on the patient's body particularly effectively and gently, particularly on those cartilage or bone areas that are sensitive to the touch of objects on the surface of the body, such as vertebrae.

In the event of possibly greater contact pressure, adverse handling by the person providing treatment, unintended movements of the patient and/or slippery coupling gel, or sweat between the front area and the body, the hollow shape prevents slipping to the side. It also ensures good geometric adaptation to protruding cartilage or bone shapes, as seen with vertebrae, for example.

The soft design protects the cartilage or bone and also the tissue over these and the skin, and couples the strokes (and optionally also the shock waves described at the beginning of this document) into the body particularly gently. Specifically, a maximum Shore hardness of 60 Sh has proven to be the most effective. The Shore hardness is the variable normally used to define the hardness of elastomers and is measured in the Shore (Sh) unit. Room temperature (23° C.) is generally assumed, and in the present case the Shore A measurement is applied.

Particularly preferably, the Shore hardness is no more than 55 Sh, 50 Sh, or 45 Sh, or even no more than just 40 Sh.

The elastomeric material of the applicator with this Shore hardness is present in the hollow shape described above (and optionally also above this shape), but according to the invention has a strength in the stroke direction of preferably 3 mm at the hollow shape in order to be able to make good use of the mechanical properties, whereby 4 mm, 6 mm, 8 mm and 10 mm are particularly preferable lower limits.

What is meant by the hollow shape described is that the central areas of the front area are depressed relative to the areas close to the edge of the front area (if the front area is facing upwards, liquid would therefore remain in the hollow shape). The geometric details will be discussed in further detail below.

Similarly to the invention described in DE 197 25 477 C and DE 20 2004 011 323 U, what is known as a ballistic mechanism is also preferred in this invention, whereby the strokes are generated by the collision of a projectile with the applicator, usually on an impact area opposite the front area on the applicator. The projectile can be accelerated in different ways, whereby a pneumatic acceleration device is particularly preferred.

In individual cases, the applicator can be made entirely out of the relatively soft elastomeric material if the coupling of shock waves in the sense of soundwaves caused by a hard collision of solid bodies is not required. However, at least two materials are preferably used for the applicator, the harder one of which forms the impact area hit by the projectile. The second material should preferably be a material that also has a minimum strength in the stroke direction of 5 mm in the impact area. The material is preferably a non-elastomeric material.

Possible materials here include, for example, metals, in particular stainless steel. In addition to this, aluminium and titanium can be cited as metallic materials, wherein both have a relatively low mass density and therefore allow relatively lightweight applicators. This can also offer the advantage that it allows stronger acceleration and therefore also a greater deflection of the travel of the applicator with the given geometry, which may be desirable in the present case. Titanium also stands out for its particularly high mechanical resilience, is therefore particularly suitable for applications with comparatively high projectile speeds and/or projectile masses. Ceramics, cf. EP 08 003 840.9/EP 2 095 843, and plastics also come under consideration, in particularly for the rotary applicator part. Plastics particularly come under consideration if less emphasis is placed on the coupling of a shock wave because, certainly where the thickness of the plastic is greater, slightly greater wave conduction losses are anticipated compared to the aforementioned materials. The same arguments apply to wood.

In the case of electromagnetic acceleration, for example, the use of primary metals is of course also possible, and the pneumatic acceleration is more flexible in this respect.

A preferred choice for the soft material of the applicator on the front area is silicone rubber, which is also tolerated well by the patient.

The applicator preferably has a rotationally symmetric shape in terms of an axis of symmetry which corresponds to the stroke direction or runs parallel thereto, whereby this axis can also be the longitudinal axis of the applicator and the acceleration direction of the projectile. The requirement for symmetry then applies at least to the visible part of the applicator, in other words to the part outside of a housing of the apparatus and therefore to the part of primary relevance to the person providing treatment and the patient. The apparatus can then be rotated without any issues during treatment, for instance.

The applicator can further have a narrowing in its front area, in other words the distal area facing the patient, and in particular can be conical and therefore have a narrowing towards the front area to correspond to the diameter or an average lateral dimension. This can be the case with a half opening angle of 10° to 15°, for instance. Preferably this will apply to the entire sheath area of the soft applicator part, in other words excluding the front area.

The soft material can, as already set out above, be held on a further applicator part made from harder material, and in particular in an undercut (relative to separating forces in the stroke direction). In particular, the material of a second applicator part with the impact area can have an undercut hollow shape into which the softer material, e.g. silicone rubber, is pressed or filled. Furthermore, a coating increasing the adhesion can also be provided in between these.

The hollow shape of the front area is preferably relatively significantly pronounced, and preferably with a depth of 10% to 30% of the average diameter of the hollow shape perpendicular to the stroke direction, whereby 25% and 15% are particularly preferred as the upper and lower limits respectively. This ensures a good anchoring in the application and good surrounding of protruding vertebrae, for example.

Furthermore, the hollow shape is preferably rounded and concave, in other words it is rounded in a section containing the stroke direction. It is particularly preferably spherical, with preferred radii of curvature of between 5 mm and 20 mm. 6 mm and 7 mm and are particularly preferred as a lower limit, 17 mm, 14 mm, 12 mm and 10 mm as an upper limit.

As the applicator is to be placed on a body with a certain amount of force, it can be advantageous not to use overly soft materials. Values of at least 10 Sh, but better at least 15 Sh or 20 Sh, are preferred.

According to a further embodiment, the applicator is held in a releasable coupling device, meaning that at least a distal applicator element (with the rotatable applicator part) can be removed forwards out of the apparatus. (To clarify: The terms "proximal" and "distal" are used from the perspective of a user of the appliance here; in other words, "distal" means a position towards the patient and "proximal" an opposed position.)

The inventors have established that the optimisation of the applicator properties in respect of certain treatments, for example changing between an applicator according to the invention and a conventional applicator, or between different applicators according to the invention, advantageously with an apparatus that is otherwise unmodified, can be performed in individual cases.

To this end, an applicator can be designed in multiple parts, wherein the removability primarily relates to a distal element. This distal element of the applicator can then be replaced with other equivalent distal applicator elements, for example because the applicator element only has a limited service life (due to the soft material, for example), because it is to be cleaned or sterilised, or because a different type of this distal applicator element (or of the whole applicator) is to be used. In particular, it is possible to use differently shaped applicator elements, possibly made from different materials, in the distal part of the applicator elements.

The replacement of the applicator is very quick and easy, preferably completely tool-free and also preferably without removing any other part of the apparatus, such as a female-end screw cap as in the conventional apparatuses of this type.

A preferred embodiment provides for an anti-rotation element for the applicator in the apparatus (not necessarily in the coupling device). Accordingly, the coupling device itself can eliminate the risk of rotation, or the risk of rotation can be eliminated by inserting an appropriately designed area of the applicator into a corresponding locking slot, particularly preferably with a multi-sided pin on the applicator side and a matching locking slot on the apparatus side, for example with a hexagonal positive fit.

The coupling can preferably also work with a positive fit which does not necessarily have to be identical to the positive fit for the anti-rotation element. In particular, a clamping sleeve can be provided which is moveable (preferably in the stroke direction) and at least pushes a positive-fit element into a corresponding locking slot on the applicator and releases it when the element is released. In particular, a housing part of the apparatus can be movable against a spring force and include or take with it the clamping sleeve. A ball is one possible positive-fit element, wherein at least two balls are preferably provided. The balls or other positive-fit elements can be exposed to force by means of an oblique area on an inside of the clamping sleeve.

The invention is explained in further detail below using an exemplary embodiment whose individual features may, within the scope of claim 1, also be material to the invention independently of each other and in other combinations.

DETAILED DESCRIPTION OF THE PREFERRED EMBODIMENT

Figure 1:
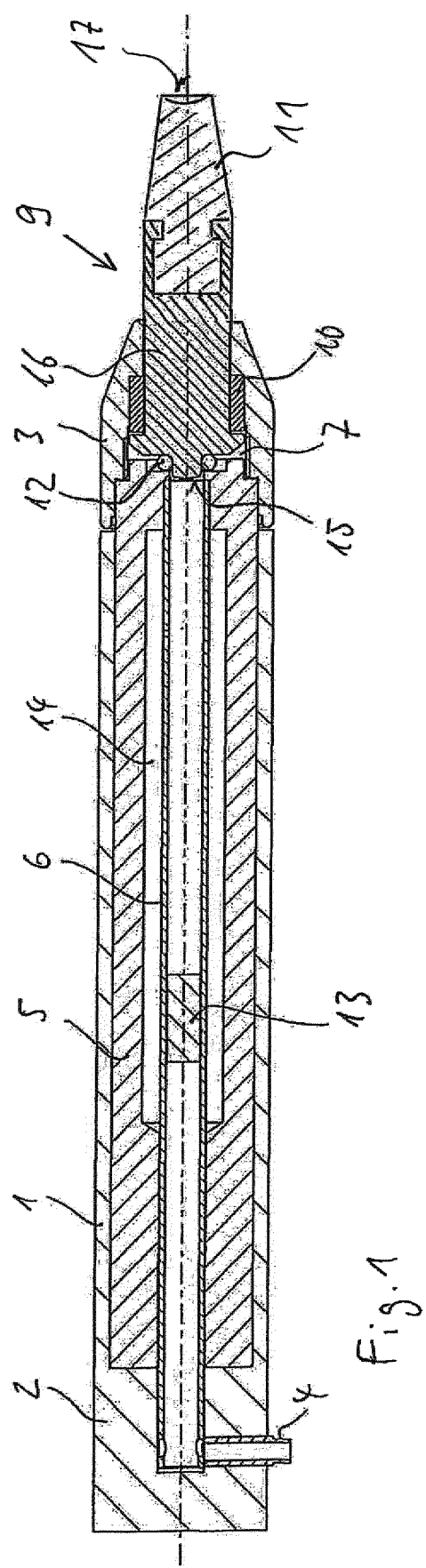
FIG. 1 shows a shock wave apparatus as a first exemplary embodiment of the invention.

FIG. 1 shows a first exemplary embodiment of the invention. It is an apparatus for coupling strokes and unfocussed (so-called radial) mechanical shock waves into the human or animal body.

A tube piece 1 forms a housing, namely together with an air inlet cap 2 pointing away from the body in the application and being integrated with the tube piece 1 and an applicator cap pointing towards the body in the application 3. The air inlet cap 2 comprises a compressed air connection 4 for a pneumatic supply. In a manner known as such, a valve controlled by a control unit, in particular a magnetic valve, is connected to this compressed air connection 4 via a pneumatic supply line, with the valve coupling compressed air pulses in a constant repetitive cycle of between, for instance, 1 Hz and 50 Hz. The valve is not shown and can also be integrated into the shown apparatus itself.

Furthermore, the apparatus is an apparatus designed to be held by hand by an operator, being connected via the aforementioned pneumatic line to a base station, not shown, with the control unit and the compressor and being placeable on the patient manually.

In the housing, a guiding tube 6 is held by an inset 5, whose end being distal to the body in the application is terminated by the air inlet cap 2 and communicates with the compressed air connection 4 there. The end of the guiding tube 6 which is proximal to the body in the application ends in a part of the insert 5, with the part projecting into the applicator cap 3 and namely ending just before the end of the insert 5 in the cap and before an inner space 7 in the applicator cap 3.

In the inner space 7 which merges into an applicator opening proximal to the body in the application, a first part of an applicator 9, shown on the left in FIG. 1, is received, with this part being made from a hard material, stainless steel in this case. Via an elastic tube element 10 made from an elastomer, it rests on a radial collar. An end of the applicator 9, pointing to the side distal to the body and containing the impact area 15, rests on the insert 5 via an O-ring 12, namely at the front face surrounding the end of the insert 5 mentioned above. This O-ring 12 is located between this front face and a collar of the applicator 9. The applicator opening 8 provides a guidance of the applicator 9 with a movability in the longitudinal direction and secures it crosswise to the longitudinal direction. The axial movability is only limited by the deformability of the elastomer element 10 and can be significantly above 1 mm relative to the remaining apparatus when operated in air.

The applicator 9 comprises, as a second part, the element 11 shown on the right in FIG. 1 which forms the very applicator part to be placed on the skin and is made from silicone rubber with a hardness of approximately 30 Sh. The applicator part 11 is cast into a hollow shape of the applicator part 16 that is undercut on the inside.

The applicator 9 is replaceable by unscrewing the applicator cap 3.

In the adjacent region of the guiding tube 6, a projectile 13 is inserted which is in contact with the applicator 9 in FIG. 1. It fits in there with a slight radial clearance (in relation to the guiding tube and the substantially cylindrical geometry of the projectile 13). The projectile 13 can be moved to-and-fro in the guiding tube 6 as a result of pressure differences in the air column in the guiding tube 6 in front of and behind the projectile (i.e. to the right and left of the projectile 13 in FIG. 1), and in particular it can be accelerated onto the applicator 9. To this end, it is accelerated from an initial position (not shown) on the left in FIG. 1 by a surge of compressed air through the compressed air connection 4 and hits the applicator 9 with its front area facing the applicator 9, namely hitting an impact area thereof facing away from the body 15.

In addition to a rebound after the collision, the backward motion of the projectile 13 is created by air flowing back from an accumulation chamber 14 surrounding the guiding tube 6 within the inset 5. The air is displaced into this accumulation chamber during acceleration of the projectile 13 towards the impact body 9 and compressed therein. When the pressure is released by the magnetic valve, there-by also venting the space behind the projectile, the projectile 13 is moved back into its initial position. In addition, or alternatively, this can also be achieved by pressurising the accumulation chamber 14 or another air volume at a side of the projectile 13 proximal to the body. The end of the guiding tube 6 that is distal to the body in the application ends at a magnet holder for the projectile 13.

It can be seen that the applicator 9 in respect of its longitudinal extension in the stroke direction consists roughly half (not including the hollow shape) of the "hard" left-hand applicator part 16 and half of the "soft" right-hand applicator part 11, wherein both have an axial length of roughly 35 mm and a maximum diameter of roughly 20 mm. Starting roughly from distal end of the hollow shape, the soft applicator part 11 narrows conically down to a diameter of roughly 15 mm over a length of roughly 15 mm (not shown to scale). The adjoining front area 17 is spherically concave with a radius of curvature of roughly 8 mm and therefore a depression in the centre (as opposed to a notional plane front area) of approximately 3 mm. The edge is rounded with a radius of 0.7 mm.

Figure 2:
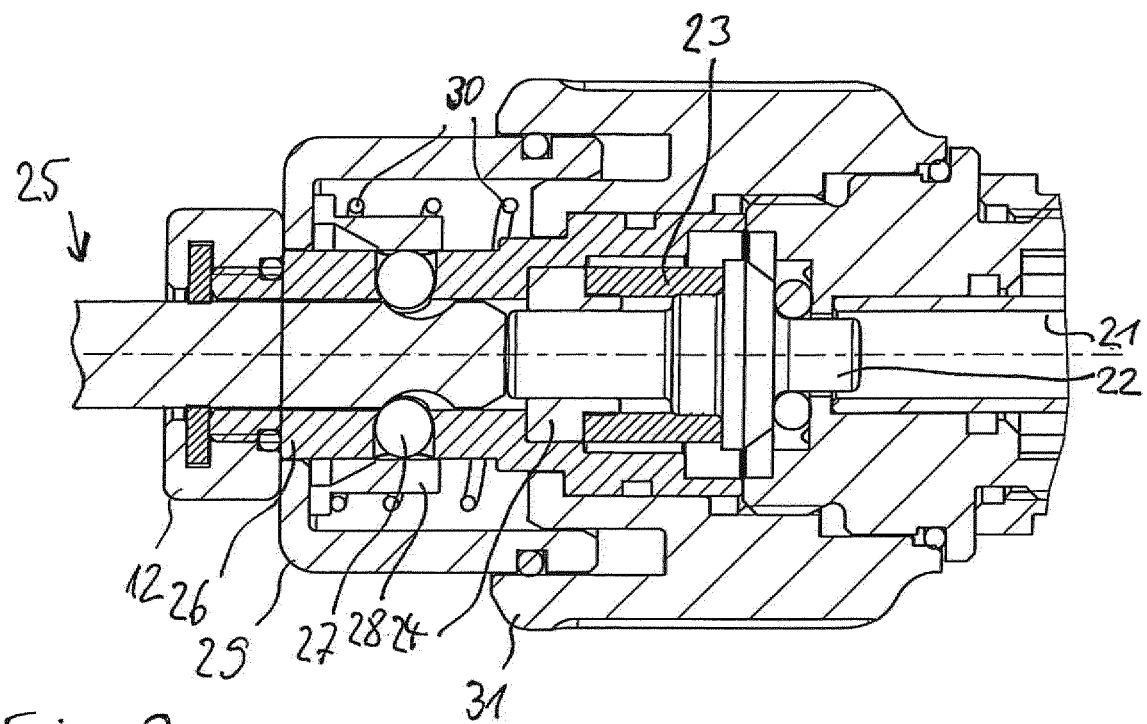
FIG. 2 shows a second exemplary embodiment, wherein the shock wave apparatus is shown only in part and with regard to an applicator coupling device not forming part of the first exemplary embodiment.
Figure 3:
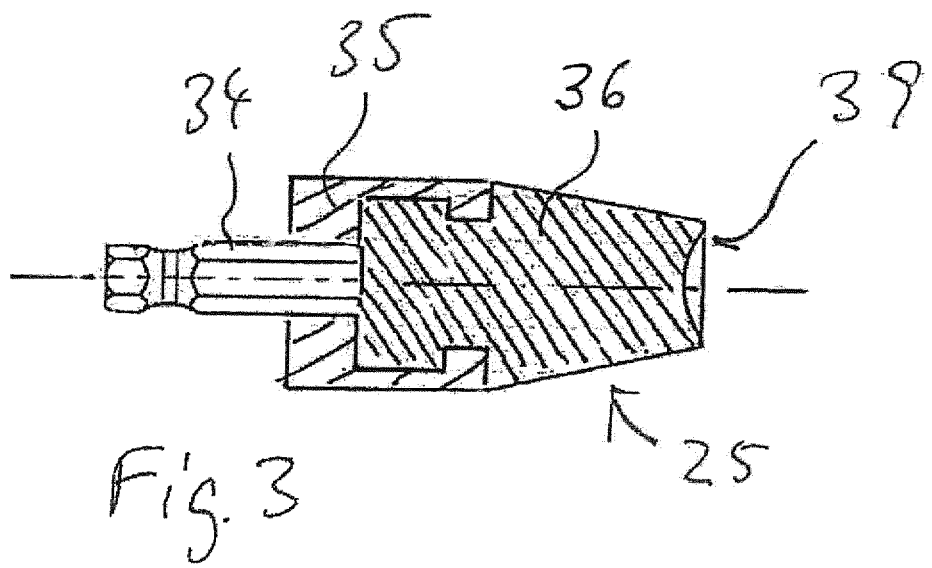
FIGS. 3 and 4 show exchangeable applicator elements for the second exemplary embodiment in FIG. 2.
Figure 4:
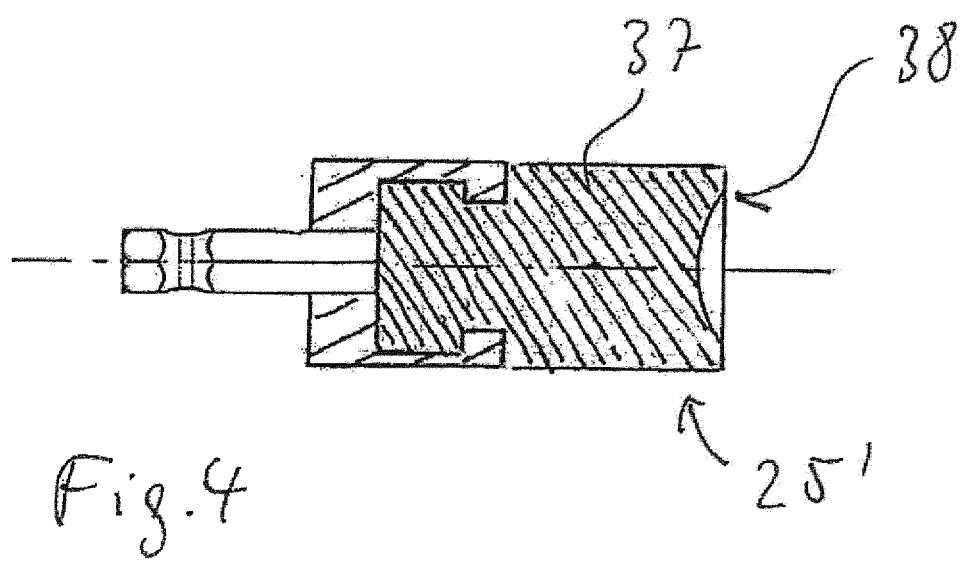

FIG. 2 shows a second exemplary embodiment wherein (with the right and left inverted compared to FIG. 1) the applicator-side end of an apparatus that otherwise corresponds to FIG. 1 is shown but is fitted with a special coupling de-vice for accommodating particularly easily changeable applicator elements. FIGS. 3 and 4 then show two applicator elements that can be used here. A word about FIG. 2 first, however: A proximal element, in other words an applicator element 22 on the right-hand side in FIG. 2, has a largely conventional shape compared to the prior art and to FIG. 1 and therefore rests with a radially enlarged flange and its distal collar side on an elastomer tube piece 23 which is deformable in the event of collisions and allows a movement in excess of one milli-metre of the proximal applicator part 22. It is also responsible for the rebound and decouples the strokes from the apparatus housing. On the distal side, this proximal applicator element 22 ends in a cylindrical pin which penetrates a guiding sleeve 24 and protrudes beyond this sleeve slightly on the distal side. In the case of conventional apparatuses, the distal front face of this pin would form the area of the applicator that comes into contact with the patient and the guiding sleeve 24 would be created in (or as) an unscrewable cap. The cap would therefore have to be removed, thus destroying a part, before the applicator (in this case the proximal applicator element 22) can be removed. The same applies to the variant from FIG. 1 with the applicator 9.

FIG. 2 further shows that the left-hand front face of the proximal applicator element 22 is in contact with the right-hand front face of a distal applicator element 25. This distal applicator element 25 will be described in more detail using FIGS. 3 and 4. It is guided into a locking slot 26, fitting positively, for instance in a hexagonal positive fit, and is therefore secured against rotation in this locking slot 26. The locking slot 26 in term must accordingly be held in the rest of the housing so that it is secured against rotation.

FIG. 2 also shows that openings for positive-fit balls 27 which mesh inwards into corresponding grooves on the outside of the distal applicator 25 are provided in the locking slot 26 (at the top and bottom of FIG. 2). These grooves are longer than necessary on the right in the figure, meaning that the entire applicator 25 and 26 can move to the left following a strike. On the other hand, the positive fit between the balls 27 and the corresponding grooves prevents the distal applicator element from falling or shooting out of the housing. The distal applicator element can in fact be pushed back into its original position as shown on the drawing after a strike simply by pressing it against the patient.

Radially outside the balls 27, a clamping sleeve 28 can be seen which evidently has an internal oblique area at its left-end end. If this clamping sleeve 28 is moved to the right out of the position shown on the drawing, the balls 27 can veer off outwards radially and the distal applicator part 25 can simply be removed from the housing as an entire entity to the left-hand side. A handy pushing in (to the right) of an externally accessible housing part 29 provides this movement of the clamping sleeve 28, wherein a coil spring 30 pushes against this and/or creates the rebound and this movable housing part 29 is movable in another part 31 of the housing and is guided constrained by an O-ring.

In FIG. 2 to the left of the movable housing part 29 used to actuate the coupling, there is also a locknut 32 which is screwed onto the receiving part 26 and is sealed against the latter by means of an O-ring and against the part 25 by means of an elastomer flat sealing ring.

Overall, it is clear that a projectile strike moves the whole applicator to the left and results in an equivalent strike movement of the distal end, not shown on the drawing, of the applicator (on the far left) towards the patient's body, wherein the coupling in of an actual shock wave will occur in parallel to this, but in many cases is not actually essential.

If the distal applicator element 25 is to be replaced, the user slides the movable housing part 29 to the right and therefore also the clamping sleeve 24, enabling the balls 27 to exit radially. The openings in the locking slot 26 for the balls 27 are also radially too narrow on the inside, preventing the balls from falling out.

FIGS. 3 and 4 show the embodiments of two distal applicator elements for the exemplary embodiment from FIG. 2. FIG. 3 shows an applicator variant 25' which, apart from the adaptation of the coupling device from FIG. 2, corresponds substantially to the applicator 9 from FIG. 1. It is designed slightly shorter, however. The multi-sided pin 34 is pressed into a stainless steel part 35 in this case, but could, in particular where the actual high-frequency soundwaves are relevant, be designed as a single piece together with the stainless steel part. Otherwise, the statements made in relation to FIG. 1 apply to the soft applicator part 36.

FIG. 4 shows a variant wherein the conical narrowing of the soft applicator part 36 is omitted and the soft applicator part 37 instead retains the maximum diameter right up to the front area. The front area 38 has a flat annular outer area and a spherical concave depression within this. The latter is slightly larger, but not necessarily deeper than the depression shown in FIG. 3; in the scenario shown in the drawing, however, the radius of curvature of 8 mm is retained.

With both exemplary embodiments, it is easy to imagine how the front area of the applicator with its depression might be placed on the back of a patient in the spinal area, for example, and pressed down, working ergonomically, without slipping off and with good surface contact thanks to its ability to adapt to the contours of the body and the material chosen. The trials carried out by the inventor have confirmed this.

The invention claimed is:

1. An apparatus for treating a human or animal body, having
    an applicator for an extraneous application onto the body,
    a housing in which said applicator is held, and
    a mechanism for generating strokes of said applicator in a stroke direction relative to the housing such that said applicator is adapted to couple said strokes into said body in an impact direction so that the mechanism is adapted to impart impacts into said body when said applicator is applied thereon,
    wherein said applicator has a front face with a concave shape facing forwardly in the impact direction and adapted for being applied onto said body, said applicator at said front face having a softness resulting from the applicator at the concave shape front face consisting of an elastomeric material having a Shore A hardness of at most 60 Sh, wherein said elastomeric material has a thickness at said concave shape of at least 3 mm in said impact direction.

2. The apparatus according to claim 1, wherein the mechanism for generating strokes comprises a projectile and a pneumatic device for accelerating said projectile in such a way that said projectile hits said applicator and generates the impacts.

3. The apparatus according to claim 2 wherein the applicator is made from a non-elastomeric material in an area hit by the projectile on impacting, and said non-elastomeric material has a minimum thickness in the impact direction of 2 mm in the area hit by the projectile.

4. The apparatus according to claim 3, wherein the applicator has, relative to the impact direction, a proximal part and a distal part, wherein the proximal part is made from the non-elastomeric material and the distal part includes the front face, and the distal part is held on or in a undercut profile, relative to the impact direction, of the proximal part, in an undercut hollow profile of the proximal part.

5. The apparatus according to claim 1 wherein the front face and a part of the applicator which is visible outside of the housing is overall rotationally symmetric around an axis parallel to the impact direction.

6. The apparatus according to claim 1 wherein the applicator has a narrowing at the front face, and is conical, along the impact direction.

7. The apparatus according to claim 1 wherein the elastomeric material of the applicator with a maximum Shore A hardness of 60 Sh is silicone rubber.

8. The apparatus according to claim 1 wherein the front face has
- a hollow shape with an average diameter of the hollow shape perpendicular to the impact direction, and
- a depth in the impact direction of between 10% and 30% of the average diameter of the hollow shape perpendicular to the impact direction.

9. The apparatus according to claim 8 wherein the hollow shape of the front face is rounded and concave, spherical and with a radius of curvature of between 5 mm and 20 mm.

10. The apparatus according to claim 8 wherein the hollow shape of the front face is surrounded by a convex edge rounded with a radius of 0.5 mm to 1.0 mm.

11. The apparatus according to claim 8 wherein the applicator has a narrowing at the front face, and is conical, along the impact direction.

12. The apparatus according to claim 11 which is designed for an impact travel in the impact direction relative to the housing of at least 1 mm.

13. The apparatus according to claim 1 wherein the elastomeric material has a maximum Shore A hardness of 60 Sh and a minimum Shore A hardness of 10 Sh.

14. The apparatus according to claim 1 wherein the applicator is held in a coupling device in the housing, wherein at least one applicator element is removable from the housing in the impact direction after releasing the coupling device.

15. The apparatus according to claim 14, wherein the applicator comprises at least two parts, whereby a distal applicator element is removable after releasing the coupling device and a proximal applicator element remains in the housing, and wherein the proximal applicator element transfers the impacts to the distal applicator element.

16. The apparatus according to claim 1 which is designed for an impact travel in the impact direction relative to the housing of at least 1 mm.

* * * * *